United States Patent [19]

Birkenstock et al.

[11] Patent Number: 5,090,997
[45] Date of Patent: Feb. 25, 1992

[54] PROCESS FOR PRODUCING POWDERED ALUMINUM ALLOYS

[75] Inventors: Udo Birkenstock, Ratingen; Jürgen Scharschmidt, Krefeld-Traar; Peter Kunert, Laufenburg; Helmut Meinhardt, Murg-Haenner; Paul Häusel, Rheinfelden/Baden; Paul Meier, Willich, all of Fed. Rep. of Germany

[73] Assignees: Bayer Aktiengesellschaft, Leverkusen; Hermann C. Starck Berlin GmbH & Co. KG, Berlin, both of Fed. Rep. of Germany

[21] Appl. No.: 639,854

[22] Filed: Jan. 11, 1991

[30] Foreign Application Priority Data

Jan. 19, 1990 [DE] Fed. Rep. of Germany ....... 4001484

[51] Int. Cl.$^5$ .............................................. B22F 9/08
[52] U.S. Cl. ......................................... 75/338; 75/351
[58] Field of Search ................. 75/338, 339, 351, 352

[56] References Cited

U.S. PATENT DOCUMENTS

| | | | |
|---|---|---|---|
| 3,293,333 | 12/1966 | Woosley et al. | 75/338 |
| 3,839,011 | 10/1974 | Larson, Jr. | 502/301 |
| 4,348,270 | 9/1982 | Bearden, Jr. | 208/9 |
| 4,760,185 | 7/1988 | Becker | 564/409 |

*Primary Examiner*—R. Dean
*Assistant Examiner*—George Wyszomierski
*Attorney, Agent, or Firm*—Sprung Horn Kramer & Woods

[57] ABSTRACT

In an advantageous process for producing powdered aluminium alloys which have a catalytic action or are capable of acting as precursors of catalysts, good results are obtained if the alloy is atomized with water and/or a gas at a temperature of 50° to 500° C. above its melting point and then cooled and dried.

8 Claims, No Drawings

PROCESS FOR PRODUCING POWDERED ALUMINUM ALLOYS

The present invention relates to a particularly advantageous process for producing powdered aluminium alloys which have a catalytic action or are precursors of catalysts.

So-called Raney metals have acquired particular significance as catalysts for hydrogenations. These can be produced, for example, by first melting together an alloy which contains the aluminium and a subgroup element, for example nickel, finely comminuting said alloy, for example in ball mills and obtaining the subgroup element originally used in catalytically active form by dissolving out the aluminium with alkalis (see, for example, Chemiker Zeitung 1975, P. 446–452).

Important catalytically active aluminium alloys are, for example, aluminium/zinc alloys which can be used, for example, in the alkylation of m-phenylenediamines (see DE-OS (German Published Specification) 3,402,983).

The catalytic action of aluminium alloys and the catalytic action of catalysts produced from aluminium alloys depends, inter alia, on the qualitative and quantitative composition of the respective aluminium alloy, but also on its particle size and particle structure.

Hitherto it has not been possible to realize all the conceivable combinations of qualitative and quantitative composition with various particle sizes and various internal and external particle structures. For example, aluminium alloys can no longer be readily ground with aluminium contents of over 50% by weight. Novel comminution methods could make it possible to realize the alloy systems specified above with particle structures which it has hitherto not been possible to obtain.

A process has now been found for producing powdered aluminium alloys which have a catalytic action or are precursors of catalysts, which is characterized in that a liquid aluminium alloy is atomized with water and/or a gas at a temperature of 50° to 500° C. above its melting point and cooled, and then any water still present is optionally removed completely or removed to a content of below 1% by weight.

Aluminium alloys with any desired content of aluminium can be used in the process according to the invention. Preferably, this is between 50 and 90% by weight, for example 55 to 95 or 58 to 90% by weight. Particularly preferred are aluminium alloys with a 60 to 90% by weight aluminium content. In addition to aluminium, the alloy may contain one or more further metals. Advantageously, these are subgroup elements such as scandium, titanium, vanadium, chromium, manganese, iron, cobalt, nickel, copper, zinc, yttrium, zirconium, niobium, molybdenum, ruthenium, rhodium, palladium, silver, cadmium, lanthanum, cerium, hafnium, tantalum, tungsten, rhenium, osmium, iridium, platinum, gold and the lanthanides.

Preferred are alloys which contain, in addition to aluminium, nickel, cobalt, molybdenum, copper, titanium, iron and/or tantalum or, in addition to aluminium, zinc. The aluminium alloys may also contain so-called promoters. For example, an alloy composed essentially of aluminium and nickel may contain further subgroup elements, for example iron, cobalt, manganese, molybdenum and/or copper, as promoters. The content of promoter metals may be, for example, 0.01 to 50% by weight, based on the total alloy. Preferably, this content is 0.05 to 10% by weight.

Aluminium alloys used in the process according to the invention may be, as described, composed qualitatively and quantitatively in a very varied manner. It is only necessary to ensure that the individual components also do in fact form an alloy, i.e. that all the components are miscible with one another in the molten state.

For the purpose of atomization, the aluminium alloy is heated to a temperature of 50 to 500° C., preferably 150° to 250° C., above its melting point. The atomization may then be carried out in devices such as those which are standard, for example, for the production of metal powders for powder-metallurgy purposes, for example in a slit orifice into which the liquid aluminium alloy is fed centrally and the atomization medium is fed concentrically thereto.

The atomization is carried out with water and/or a gas. If the liquid aluminium alloy is fed in a quantity of 10 to 50 kg/min to the atomization device, it is possible to use, for example, per kg of aluminium, 5 to 15 l of water with a pressure of, for example, 10 to 500 bar or, for example, per kg of aluminium alloy, 0.5 to 10 $m^3$ of gas with a pressure of, for example, 2 to 100 bar. The following quantity combinations are preferred: 15 to 40 kg/min of liquid aluminium alloy, 6 to 12 l of water with a pressure of 20 to 400 bar or 1 to 8 $m^3$ of gas with a pressure of 5 to 80 bar per kg of aluminium alloy. Here and in the following $\times m^3$ of gas means $\times m^3$ of gas measured at the actual pressure in the atomization device.

Suitable gases for the atomization are, for example, those which contain 1 to 35% by weight of oxygen. In addition to oxygen, for example substantially or completely inert gases such as nitrogen and/or noble gases may be present. Preferably, gases are used in the atomization which contain 5 to 25% by weight of oxygen, air being particularly preferred. Oxygen-free gases, for example nitrogen or argon, may also be used.

The atomization with water yields predominantly rough particles with fine inner textural structure, while the atomization with gas yields predominantly spherical to irregular particles with coarse textural structure. The type of atomization and the quantities, to be used in it, of aluminium alloy, atomization media and compositions of atomizing media which yield an optimum result for a particular aluminium alloy and its use for a particular catalytic process or as a precursor for a catalyst for a particular catalytic process can, if necessary, be determined for a specific individual case by routine serial tests.

The atomization is followed by a cooling. This can be carried out, for example, with water or a gas. If water is used, the atomized aluminium alloy can be introduced, in the simplest case, from the top into a sufficiently tall vessel filled with water or with water flowing through it. The atomized alloy then cools while sinking. If a gas, for example, air, is used, it can be conveyed, for example, in countercurrent to the falling particles of atomized aluminium alloy.

After cooling with water, the temperature of the atomized aluminium alloy may, for example, be below 50° C. Preferably it is then 10° to 30° C. After cooling with air, the temperature of the atomized aluminium alloy may, for example, be below 100° C. Preferably, it is then below 50° C., in particular 30° to 48° C. Aluminium alloys of the type described above, which have been atomized and cooled in the manner according to the invention, are in general stable on storage if their water content is below 1% by weight, preferably below 0.1% by weight. Such low water contents are generally spontaneously established if the cooling is carried out with dry air. However, if the cooling is carried out with water, the atomized, cooled aluminium alloy must furthermore be dried in order to obtain a product which is stable on storage. In this case, the procedure is such that a dry gas is used in a quantity of, for example, 1 to 10 m³/kg of aluminium alloy and, if necessary the material to be dried is turned over during drying. If a product which is stable on storage is not required, for example because it is desired to use it immediately as a catalyst or to produce a catalyst from it immediately, the drying can, of course, be omitted.

The powdered aluminium alloys produced according to the invention are remarkable for the fact that they are particularly active catalysts or that particularly active catalysts, for example those of the Raney type, can be produced from them. In particular, powdered aluminium alloys according to the invention having a high aluminium content can be produced in a simple manner. Thus, particle structures and catalysts can be obtained which were not previously accessible.

Insofar as the powdered aluminium alloys produced according to the invention are catalysts, for example are aluminium-zinc alloys, they can be used for the alkylation of aromatic compounds, for example for the alkylation of phenols, anilines or phenylenediamines. Insofar as the powdered aluminium alloys produced according to the invention are precursors of catalysts, for example are aluminium alloys which contain nickel, cobalt, iron and/or manganese, catalysts can be produced from them, for example by treatment with alkalis, which are suitable for hydrogenations. Examples of such hydrogenations are the conversion of unsaturated hydrocarbons into less unsaturated or saturated hydrocarbons, the conversion of nitriles into amines and the conversion of nitro groups, in particular nitro groups bound to aromatic systems, into amine groups.

EXAMPLES

EXAMPLE 1 a) Production and atomization of an alloy 60 kg of nickel and 140 kg of aluminium were melted in an induction furnace. After reaching the liquidus temperature, the melt obtained was heated further to 1200° C. and then poured out of the induction furnace into a heated discharge funnel having a base outlet of 18 mm diameter. The jet of liquid metal emerging from this funnel was intercepted with a concentrically arranged annular water jet at 30 bar and atomized. The atomization time was 10 minutes and the quantity of water supplied 2 m³. The atomized powder was collected in a 2 m high water tank situated below the atomization system and cooled. The temperature of the atomized alloy removed from the tank was 23° C. The residual moisture (19% by weight of water) was substantially removed in a dry, heated 4000 m³/h airstream within 20 minutes.

In this way, 195 kg of alloy powder having the following analysis were obtained: 29.5% by weight of nickel, 69.7% by weight of aluminium, 0.4% by weight of oxygen and 0.05% by weight of water.

The powder obtained had a predominantly rough particle shape, and the particle distribution obtained was:

| | |
|---|---|
| over 400 μm | 5.5% by weight |
| 200 to 400 μm | 28.1% by weight |
| 100 to 200 μm | 41.6% by weight |
| 50 to 100 μm | 18.9% by weight |
| below 50 μm | 5.9% by weight |

The powder obtained was stable on storage and it was possible to handle it without problems.

b) Production of a catalyst 782 g of sodium hydroxide were dissolved in 3129 g of water in a beaker. The temperature of the sodium hydroxide solution obtained in this way was adjusted to 80° C. The air above the solution was replaced by nitrogen and work was carried out under a nitrogen blanket during the entire reaction time.

200 g of the powdered alloy obtained in accordance with a) were then added to the sodium hydroxide solution in portions of 6 g each. The powdered alloy was added over a time period of 20 minutes, the temperature of the sodium hydroxide solution being kept at 80±2° C. in order not to allow the foam formation to become too intense.

After the 200 g of powdered alloy had been introduced, the reaction mixture was stirred for a further 30 minutes at 80° C. Then the mother liquor was decanted from the catalyst formed and the catalyst was post-treated with a solution of 78 g of sodium hydroxide in 313 g of water for 5 minutes while stirring. This washing liquor was then separated off by decanting and the catalyst was washed with water to a pH of 8.0.

59 g of catalyst (100%), produced as an aqueous slurry, were obtained.

c) Use of the catalyst 200 g of phenol and 10 g of the catalyst (100%) obtained in accordance with b) were hydrogenated at 230° C. and 150 bar hydrogen pressure in a 0.7 l autoclave having a stirrer and electrical external heating. In a reaction time of 12 minutes, a mixture was obtained which, ignoring the reaction water, contained 97.4% by weight of cyclohexanol, 2.3% by weight of cyclohexane and 0.3% by weight of other byproducts.

EXAMPLE 2 a) Production and atomization of an alloy 1 kg of nickel, 12.4 kg of iron and 122.8 kg of aluminium were melted in an induction furnace. After reaching the liquidus temperature, the melt obtained was heated further to 1300° C. and then poured out of the induction furnace into a heated ceramic casting funnel having a centrally arranged bottom outlet. The 15 mm diameter liquid metal jet emerging from the bottom outlet was atomized with compressed air at 6.2 bar which was fed through a concentrically arranged annular gap nozzle. The atomization time was 11 minutes and the air usage 1000 m³ (measured at 6.2 bar). The atomized powder was collected in a water tank below the atomization system. The temperature of the atomized alloy removed from the tank was 21° C.

The powder, pre-dehydrated by means of a suction filter and having a residual moisture content of 18% by weight of water, was dried in a stream of dry and slightly heated air at 4200 m³/h within 24 minutes. The residual moisture content was then only 0.03% by weight of water. In this way, 199.4 kg of alloy powder with the following analysis were obtained: 33.9% by weight of nickel, 5.72% by weight of iron, 59.8% by weight of aluminium and 0.39% by weight of oxygen.

The powder obtained had a predominantly spherical particle shape and had the following particle distribution:

| over 400 μm | 12.6% by weight |
|---|---|
| 200 to 400 μm | 37.3% by weight |
| 100 to 200 μm | 35.2% by weight |
| 50 to 100 μm | 11.6% by weight |
| below 50 μm | 3.3% by weight | b) Production of a catalyst

The alloy powder obtained in accordance with a) was converted into a catalyst as described in Example 1b). 79 g of 100% catalyst, produced as an aqueous slurry, were obtained.

c) Use of the catalyst 80 g of a mixture of 65% by weight of 2,4- and 35% by weight of 2,6-dinitrotoluene and 240 g of methanol were introduced into a 0.7 l autoclave having a stirrer and electric external heating and were hydrogenated with 10 g of catalyst (100%) obtained in accordance with b) at 100° C. and 100 bar hydrogen pressure. In a reaction time of 14 minutes, the dinitrotoluenes were virtually quantitatively reacted and the corresponding diamines, and also 0.13% by weight of N-alkyl compounds as byproducts, were obtained.

The greater activity of this catalyst compared with those of the prior art is exhibited, in particular, in the shorter time which is necessary for its production.

EXAMPLE 3 a) Production and atomization of an alloy 71 kg of nickel, 12.4 kg of iron and 122.8 kg of aluminium were melted in an induction furnace. After reaching the liquidus temperature, the melt obtained was heated further to 1300° C. and then fed to an atomization system via a ceramic casting funnel with a centrally arranged bottom outlet. The 15 mm diameter jet of liquid metal emerging from the bottom outlet block of the funnel was atomized with compressed air at 6.2 bar which was fed through a concentrically arranged annular gap nozzle, water being sprayed into the atomized powder below the annular gap nozzle from a spraying ring. The atomization time was 11 minutes and the air usage 1000 m³ (measured at 6.2 bar). The atomized powder was collected in a water tank below the atomization system. The temperature of the powder removed from the tank was 21° C. The powder, pre-dehydrated by means of a suction filter and having a residual moisture content of 18% by weight of water, was dried in a 4200 m³/h airstream of pre-heated dry air within 24 minutes. The residual moisture content of the dried material was only 0.03% by weight of water. In this way, 199.4 kg of alloy powder having the following analysis were obtained: 33.9% by weight of nickel, 5.72% by weight of iron, 59.8% by weight of aluminium and 0.39% by weight of oxygen.

The powder obtained had a predominantly spherical particle shape and had the following particle distribution:

| above 400 μm | 12.6% by weight |
|---|---|
| 200 to 400 μm | 37.3% by weight |
| 100 to 200 μm | 35.2% by weight |
| 50 to 100 μm | 11.6% by weight |
| below 50 μm | 3.3% by weight | b) Production of a catalyst

The alloy powder obtained in accordance with a) was converted into a catalyst as described in Example 1b). 79 g of 100% catalyst, produced as an aqueous slurry, were obtained.

c) Use of the catalyst

A dinitrotoluene mixture was hydrogenated in the same way as in Example 2c) with the catalyst obtained in accordance with b). The results were equivalent to those of EXAMPLE 2c).

EXAMPLE 4 a) Production and atomization of an alloy 2.31 kg of nickel, 2.31 kg of tantalum and 18.5 kg of aluminium were melted in an induction furnace. The mixture was heated to the liquidus point and subsequently to 1200° C. under argon at 1000 mbar, and it was then poured into a pre-heated casting funnel which had a 7 mm diameter outlet opening symmetrically at the bottom. The emerging jet of liquid metal was atomized with argon by means of a concentrically arranged annular gap nozzle. The gas pressure was 6.8 bar, the atomization time was 90 seconds and 33.9 m³ (measured at 6.8 bar) of argon were used.

The atomized alloy was cooled in an argon stream over a free-fall height of 4.5 m. The temperature of the powder obtained was 35° C.

In this way, 19.4 kg of alloy powder having the following analysis were obtained: 10.1% by weight of nickel, 8.3% by weight of tantalum, 0.03% by weight of oxygen and 81.5% by weight of aluminium. It was not possible to detect any residual moisture content in this alloy powder.

The powder obtained had an almost exclusively spherical particle shape and the particle distribution was as follows:

| over 150 μm | 21.4% by weight |
|---|---|
| 106 to 150 μm | 13.8% by weight |
| 52 to 106 μm | 23.2% by weight |
| below 53 μm | 41.6% by weight | b) Production of a catalyst

The alloy powder obtained in accordance with a) was converted into a catalyst as described in Example 1b). 40 g of 100% catalyst, produced as an aqueous slurry, were obtained.

c) Use of the catalyst

An autoclave with 80 ml liquid capacity and provided with a gasification stirrer, a hydrogen inlet line, an inlet tube for the aromatic dinitro compound whose lower end terminated immediately next to the gasification stirrer, and an outlet valve for excess hydrogen was used. The reaction mixture composed of an aromatic diamine and water left the autoclave through a frit which retained the catalyst. This apparatus made it possible to continuously hydrogenate aromatic dinitro compounds until the catalyst was completely exhausted. The temperature in the autoclave was regulated by an external heating and cooling circuit and a cooling coil in the interior of the reactor.

80 ml of a mixture of (i) a mixture of 80% by weight of 2,4- and 20% by weight of 2,6-diaminotoluene with (ii) water in a ratio by weight of (i) : (ii)=63:37, in which 1.6 g of catalyst obtained in accordance with b) was suspended, were introduced into the autoclave. Then the contents of the autoclave were heated up to 190 to 200° C. under a hydrogen pressure of 15 bar. At this temperature, 64 l of hydrogen and, by means of a proportioning pump, 53 g of a mixture of 80% by weight of 2,4- and 20% by weight of 2,6-dinitrotoluene were fed into the autoclave hourly, during which process the temperature in the reactor rose to 215° C. Hydrogenation was carried out at this temperature and at a pressure of 20 bar until the catalyst was exhausted (50 hours), the resultant process product (a mixture of diamine and water) being continuously removed. The yield of diaminotoluene was equivalent to 98.7% of theory, based on the dinitrotoluenes used. In addition, 1.1% by weight of tar-like byproducts and 0.2% by weight of so-called low boilers were produced.

Compared with those of the prior art, the catalyst used in this manner exhibited an equally good selectivity at higher working temperature. The higher working temperature makes it possible to remove the heat of reaction at higher temperature level and is consequently more economical.

In addition, it was not possible to grind an alloy such as was melted in accordance with a) in the induction furnace, in rather large pieces after cooling in the conventional way in a screen ball mill.

EXAMPLE 5 a) Production and atomization of an alloy 16.1 kg of zinc and 140.2 kg of aluminium were melted in an induction furnace. After reaching the liquidus temperature, the melt was heated further to 810° C. and then poured into a heated discharge funnel having a 12 mm diameter bottom outlet. The molten jet of metal emerging from the bottom outlet was atomized with water in a concentrically arranged annular gap nozzle. The water was supplied at a pressure of 52 bar, the amount of water fed in was 1800 l and the atomization time was 5 minutes. The atomized powder was collected in a water tank situated below the atomization system and cooled during the process to 24° C.

The material taken from the tank had a residual moisture content of 18% by weight of water and was dried in a 3200 m³/h dry hot air stream within 15 minutes.

In this way, 153.5 kg of alloy powder having the following analysis were obtained: 9.7% by weight of zinc, 0.24% by weight of oxygen, 0.08% by weight of water and 89.7% by weight of aluminium.

The powder obtained had a rough to rounded particle shape and the particle distribution obtained was:

| above 400 μm | 1.2% by weight |
| 200 to 400 μm | 12.3% by weight |
| 100 to 200 μm | 34.5% by weight |
| 50 to 100 μm | 30.1% by weight |
| below 50 μm | 21.9% by weight |

The powder obtained was stable on storage and it was possible to process it further without problems.

b) Use of the catalyst 250 g of toluylenediamine (a mixture of 65% by weight of 2,4- and 35% by weight of 2,6-toluylenediamine) were heated with 4.7 g of the alloy powder obtained in accordance with a) and 8.3 g of aluminium chloride (anhydrous) to 180° C. while stirring. At 130° C., the evolution of hydrogen began and this had terminated after 35 minutes.

The reaction mixture was then reacted with ethylene in a stirred autoclave at temperatures of 250° to 280° C. and at a pressure of 150 to 180 bar. The ethylene take-up had terminated after 25 minutes.

After working-up with aqueous sodium hydroxide solution, an alkylation product was obtained which, according to gas chromatographic analysis, contained 98% of dialkylated toluylenediamines.

The higher activity of the catalyst used compared with those of the prior art emerges from the lower temperatures, shorter times and lower pressures which have to be used.

EXAMPLE 6 a) Production and atomization of an alloy 99 kg of aluminium and 98 kg of nickel were melted in an induction furnace. After reaching the liquidus temperature, the melt obtained was heated further to 1530° C. and then atomized by means of a ceramic funnel with a bottom outlet arranged in the center. The 12 mm diameter liquid jet of metal emerging from the bottom discharge block was atomized with 4.7 bar compressed air which was fed in through a concentrically arranged annular gap nozzle. The atomization time was 8.2 minutes and the air consumption 1150 m³ (measured at 4.7 bar). The atomized powder was collected in a water tank below the atomization system and removed therefrom at a temperature of 22° C. The powder, predehydrated by means of a suction filter, had a residual moisture content of 17% by weight of water which was substantially removed in a 4000 m³/h airstream of preheated dry air within 20 minutes.

In this way, 189.5 kg of alloy powder having the following analysis were obtained: 49.6% by weight of nickel, 49.3% by weight of aluminium, 0.65% by weight of oxygen and 0.04% by weight of water.

The powder obtained had a predominantly spherical particle shape and the particle distribution obtained was:

| above 400 μm | 16.5% by weight |
| 200 to 400 μm | 38.6% by weight |
| 100 to 200 μm | 33.8% by weight |
| 50 to 100 μm | 9.6% by weight |
| below 50 μm | 1.5% by weight | b) Production of a catalyst

A catalyst was produced in a corresponding manner to that described in Example 1b) from the powder obtained in accordance with Example 6a) with the aid of 500 g of sodium hydroxide and 2000 g of water. 100 g of catalyst (100%), produced as an aqueous sludge, were obtained.

c) Use of the catalyst

Virtually the same hydrogenation results were obtained as those in Example 1c) using the catalyst obtained in accordance with Example 6b). Here again, the higher activity of the catalyst compared with those of the prior art was revealed, in particular, in the shorter time which was necessary for its production.

We claim:

1. A process for producing powdered aluminum alloys which can be used as catalyst for alkylating aromatic compounds and/or can be treated with alkalis to form hydrogenation catalysts comprising
   a) atomizing a liquid aluminum alloy using an atomizer device in the presence of water or a mixture of water and a gas at a temperature of 50 to 500° C. above its melting point,
   b) cooling the atomized alloy, and
   c) removing the water present to a content of below 1% by weight.

2. The process of claim 1, in which the aluminum alloy contains 50 to 99% by weight of aluminum.

3. The process of claim 1, in which the aluminum alloy contains one or more subgroup elements selected from the group consisting of scandium, titanium, vanadium, chromium, manganese, iron, cobalt, nickel, copper, zinc, yttrium, zirconium, niobium, molybdenum, ruthenium, rhodium, palladium, silver, cadmium, lanthanum, cerium, hafnium, tantalum, tungsten, rhenium, osmium, iridium, platinum, gold and the lanthanides.

4. The process of claim 1, in which the atomization is carried out at a temperature of 150° to 250° C. above the melting point of the aluminum alloy.

5. The process of claim 1, in which 5 to 15 l of water are used for the atomization per kg of the aluminum alloy.

6. The process of claim 1, in which 0.5 to 10 $m^3$ of gas (measured at the pressure in the atomization device) are used for the atomization per kg of the aluminum alloy.

7. The process of claim 1, in which the temperature after cooling is below 50° C.

8. The process of claim 1, in which any water remaining after cooling is substantially completely removed.

* * * * *